United States Patent [19]

Koike et al.

[11] Patent Number: 5,187,067
[45] Date of Patent: Feb. 16, 1993

[54] IMMUNOLOGICAL DETERMINATION OF FREE HUMAN PROTEIN S AND C4BP-PROTEIN S COMPLEX

[75] Inventors: Yukiya Koike; Kenji Wakabayashi; Yoshihiko Sumi, all of Hino; Yataro Ichikawa, Tokorozawa, all of Japan

[73] Assignee: Teijin Limited, Osaka, Japan

[21] Appl. No.: 670,383

[22] Filed: Mar. 14, 1991

Related U.S. Application Data

[63] Continuation of Ser. No. 132,886, Dec. 9, 1987, abandoned.

[30] Foreign Application Priority Data

Dec. 15, 1986 [JP] Japan .................................. 61-296766
Dec. 17, 1986 [JP] Japan .................................. 61-298881

[51] Int. Cl.⁵ .................... C07K 15/00; C07K 3/18; G01N 33/53; C12N 5/18
[52] U.S. Cl. .................................. 435/7.9; 436/821; 436/824; 530/387.1; 530/388.25; 530/412; 530/413; 435/240.27; 435/7.1
[58] Field of Search .............. 436/500, 541, 507, 518, 436/535, 548; 530/387, 412, 413, 388.25; 435/240.27, 7.1, 7.9

[56] References Cited

U.S. PATENT DOCUMENTS 4,486,530 12/1984 David et al. ........................... 435/7

FOREIGN PATENT DOCUMENTS 0045103 2/1982 European Pat. Off. .
0128696 12/1984 European Pat. Off. .

OTHER PUBLICATIONS

Dahlbaeck et al., *Chemical Abstracts*, vol. 94(25):2069799 (1981).
Sugimoto et al., *Chemical Abstracts*, vol. 106(11):80566j (1987).
Bertina et al., *Chemical Abstracts*, vol. 103(1), 2587r (1985).
Kohler et al., *Nature*, vol. 256, pp. 495-497, Aug. 7, 1975.
Malm et al., *European Journal of Biochemistry*, vol. 165, pp. 39-45 (1987).
Fudenberg et al. (ed.), *Basic and Clinical Immunology*, 3rd edition, pp. 360, 361 and 739, Lange Medical Pub., Los Altos, CA (1980).
Bertina et al., *Thrombosis and Hemostasis*, vol. 53(2), pp. 268-272 (1985).
Litwiller et al., Chemical Abstracts 105:22743h (1986).
Jenny et al., Chemical Abstracts 105:186874c (1986).

*Primary Examiner*—David L. Lacey
*Assistant Examiner*—Lila Feisee
*Attorney, Agent, or Firm*—Wenderoth, Lind & Ponack

[57] ABSTRACT

A method of immunologically determining free human protein S in an assay sample, which comprises contacting a primary antibody fixed to an insoluble solid carrier and a labelled secondary antibody with the assay sample, the primary and secondary antibodies having the property of binding to different epitopes of free human protein S, and one of the primary and secondary antibodies being a monoclonal antibody having the property of not binding to a complex of the human protein S and human complement cofactor C4b-binding protein (C4bp) but specifically binding to the free human protein S. Also provided is a method of immunologically determining a complex of human protein S and human complement cofactor C4b-binding protein (C4bp) in an assay sample, which comprises contacting a primary antibody fixed to an insoluble solid carrier and a labelled secondary antibody with the assay sample, one of the primary and secondary antibodies being a monoclonal antibody having the property of not binding to free human protein S and human complement cofactor C4b-binding protein (C4bp) but binding specifically to the complex, and the other being an antibody having the property of binding to the human complement cofactor C4b-binding protein (4Cbp).

14 Claims, 4 Drawing Sheets

IMMUNOLOGICAL DETERMINATION OF FREE HUMAN PROTEIN S AND C4BP-PROTEIN S COMPLEX

This application is a continuation of now abandoned application, Ser. No. 07/132,886 filed Dec. 9, 1987.

This invention relates to the determination of free human protein S or a complex of human protein S and human complement cofactor C4b-binding protein (C4bp) in an assay sample. More specifically, it relates to a method of immunological determination of free human protein S or the aforesaid complex in an assay sample by the "sandwich" technique using a novel specific monoclonal antibody which binds to free human protein S or the aroresaid complex, a novel antibody that can be used in the above method, a reagent system used in the above method, and the use of the novel monoclonal antibody in the separation and recovery of free human protein S.

Protein S, like protein C, is a vitamin K-dependent protein. It was first isolated by Discipio et al. from bovines and humans in 1977 [se Discipio, R. G., Hermodson, M. A., Yates, S. G. and Davie, E. M.: Biochemistry, 16, 696–706 (1977)].

Protein S is a single-chain glycoprotein having a molecular weight of 69,000 (human) which is contained in an amount of about 10 mg/liter in a normal human plasma sample. Its structure is very similar to those of other vitamin K-dependent factors, and it has about 10 gamma-carboxyglutamic acid (Gla) moieties at the $NH_2$ terminus. Protein S exists in two forms in the blood. One is free protein S which acts as a cofactor of activated protein C. The other is a complex of protein S and complement cofactor C4b-binding protein (C4bp), in which protein S is non-covalently bonded to high-molecular C4b binding protein (C4bp), a control factor in a complement system (the complex will be abbreviated sometimes as "C4bp-protein S complex"). The ratio of free protein S to C4bp-protein complex is about 1:1.

The importance of the function of protein S in the C4bp-protein S complex is that it has a very strong affinity for a negatively charged surface of a phospholipid [Nelsestuen, G. L., Kisiel, W. and Discipio, R. G.: Biochemistry, 17: 2134–2138 (1978)]. It is believed that when a cell is damaged or activated, the Gla-domain in protein S binds to the phospholipid in the presence of $Ca^{2+}$, and C4bp further binds to protein S to form a complex, whereby the protein S performs its function Dahlback, KB: Semin. Thromb. Haemostat., 10, 139-148 (1984)].

Recent studies have shown that protein S plays a very important role in the mechanism to controlling the coagulation and fibrinolysis system of protein C, and its physiological significance in relation to thrombosis has aroused interest. It was reported that the congenital deficiency of protein S could be a cause of thrombosis [Comp. P. C., Nixon, R. R., Cooper, N. R. and Esmon, C. T.: J. Clin. Invest., 74: 2082-2088 (1984)].

If it is possible to elucidate the mechanism of action of protein S and to measure the amounts of antigen and activity of protein S in blood, it would have a very important significance in the fields o; basic medicine and clinical medicine.

On the other hand, monoclonal antibodies have recently gained widespread use for analysis of the functions and structures of antigen proteins or for immunoassays (EIA, RIA) because of the advantage that they are specific only for a single epitope and monoclonal antibodies having the same specificity can be produced stably. Particularly, for the functional and molecular analysis of antigen proteins, it would be desirable to discover an antibody which recognizes a site that is involved in the function of the antigen proteins or their special structural sites.

Conventional methods for determining protein S include, for example, the Laurell method using an antiserum to protein C, and RIA (radioimmuoassay) and EIA (enzyme immunoassay) involving the use of polyclonal antibodies. These methods, however, permit measurement of only the total amount of free protein S and its complex with C4bp. The former method has the disadvantage that animal antisera having a fixed activite are extremely difficult to obtain stably in large amounts, and the activity of the sera must be corrected by using a standard substance. It also has the defect that a long period of time is required for immunodiffusion. According to the latter methods, antibodies must be purified from anti-sera, and stable antibodies are difficult to obtain steadily.

The present inventors noted that protein S forms a complex with complement cofactor C4b-binding protein, C4bp, and thought that if a monoclonal antibody which binds selectively only to free protein S and a monoclonal antibody which binds selectively only to the C4bp-protein S complex can be obtained, it would be possible to, perform selective immunological determination of free protein S and C4bp-protein S complex simply and accurately without the defects of the prior art. Extensive investigations based on this thought have now led to the successful creation of specific monoclonal antibodies.

According to one aspect of this invention, there is provided a method of immunologically determining free human protein S in an assay sample, which comrises contacting a primary antibody fixed to an insoluble solid carrier and a labelled secondary antibody with the assay sample, the primary and secondary antibodies having the property of binding to different epitopes of free human protein S, and one of the primary and secondary antibodies being a monoclonal antibody having the property of not binding to a complex of the human protein S and human complement cofactor C4b-binding protein (C4bp) but specifically binding to the free human protein S.

According to another aspect of this invention, there is provided a method of immunologically determining a complex of human protein S and human complement cofactor C4b-binding protein (C4bp) in an assay sample, which comprises contacting a primary antibody fixed to an insoluble solid carrier and a labelled secondary antibody with the assay sample, one of the primary and secondary antibodies being a monoclonal antibody having the property of not binding to free human protein S and human complement cofactor C4b-binding protein (C4bp) but binding specifically to said complex, and the other being an antibody having the property of binding to the human complement cofactor C4b-binding protein (C4bp).

The method of immunologically determining a specific anti9en in an assay sample using a primary antibody fixed to an insoluble solid carrier and a labelled secondary antibody is called the "sandwich method" and is described for example, in Wide "Radioimmunoassay Methods", 199-206 (1970).

The methods provided by this invention are characterized by the fact that based on the principle of the sandwich method, one of free human protein S and C4bp-protein S complex in an assay sample is selectively determined by using the following monoclonal antibodies newly created by the present inventors.

(a) A monoclonal antibody having the property of not binding to C4bp-protein S complex but specifically binding to free human protein S (to be referred to as "monoclonal antibody A" for the sake of convenience in the present specification).

(b) A monoclonal antibody having the property of not binding to free human protein S and C4bp but specifically binding to C4bp-protein S complex (to be referred to as "monoclonal antibody B" for the sake of convenience in the present specification).

These methods of the invention permit measurement of free human protein S or C4bp-protein S complex in an assay sample (for example, plasma) with consistently good accuracy without variations in the quality of reagents. According to the methods of this invention, free human protein S and C4bp-protein S complex can be measured directly, and accurate measurement within short periods of time can be carried out without any influence of foreign materials in the sample.

The determination methods of this invention thus permit diagnosis of the conditions of rhrombosis having cancer as a basic disease, nephrosis, etc., and accurate determination of the fibrinolytic state of toxemia of pregnancy and the fibrinolytic state or patients having undergone surgical operation, which have heretofore been substantially impossible. This offers great advantages to medicine.

The invention will now be described in greater detail.

(1) Determination of free human protein S in an assay sample by using the monoclonal antibody A:

In the method of immunologically determining free human protein S in an assay sample according to this invention, one (primary antibody) of the two antibodies is fixed to an insoluble solid carrier, and the other (secondary antibody) is used in the labelled state. The monoclonal antibody A may be used as the primary antibody fixed to the insoluble solid carrier, or as the labelled secondary antibody. In either case, there is substantially no effect on the results of determination of human protein S.

The antibody used in combination with the monoclonal antibody A may be any monoclonal or polyclonal antibody which recognizes an epitope of human protein S different from that recognized by the monoclonal antibody A and binds to it. Generally, however, it is convenient to use a monoclonal antibody which recognizes and binds to an epitope of free human protein S different from that recognized by the monoclonal antibody A, and which is produced from a hybridoma obtained as a by-product during screening of a hybridoma producing the monoclonal antibody A.

The primary antibody may be fixed to the insoluble solid carrier by methods known per se. For example, a solution of the primary antibody and the insoluble solid carrier are contacted and left to stand, whereby the antibody is physically adsorbed on the carrier. It is also possible to combine the functional groups of the antibody, such as a carboxyl, amino or hydroxyl group, chemically with the insoluble solid carrier. Preferably, the surface of the carrier to which the primary antibody has been fixed is coated with a suitable substance such as bovine seru albumin in order to avoid non-specific combination with the secondary antibody or the assay sample.

Examples of the insoluble solid carrier used to fix the primary antibody include polymeric materials such as polystyrene, polyethylene, polypropylene, polyesters, polyacrylonitrile, fluorine-containing resins, nitrocellulose, crosslinked dextran, polysaccharides and agarose, inorganic materials such as glass and metal, and combinations of these. The solid carrier may be in various shapes, for example in the shape of a tray, sphere, fiber, particle, bead, disc, rod, receptacle, cell or test tube. Specific examples of the insoluble solid carrier are plastic receptacles, plastic beads, glass beads and metal particles.

The secondary antibody is labelled with radioisotopes, enzymes or luminescent substances. Examples of the radioisotopes are $^{125}I$, $^{131}I$, $^{14}C$ and $^3H$. Examples of the enzymes are alkaline phosphatase, peroxidase, and beta-D-galactosidase. Examples of the luminescent substances are fluorescein isothiocyanate and tetramethyl rhodamine isothiocyanate. These are merely illustrative, and other labelling substances used in immunological assays may also be used. Combination of the labelling substances with the secondary antibody may be effected by methods known per se, for example by the methods described in G. S. David: Biochem. Biophys. Res. Commun., 48, 464–471 (1972), M. Imagawa et al., Anal. Lett., 16, 1509–1523 (1983) and M. Nishioka et al , Cancer Res., 32, 162–166 (1972).

The fixed primary antibody and the labelled secondary antibody are then brought into contact with an assay sample for determination of human protein S by a two-step method comprising contacting the sample first with the fixed primary antibody and than with the labelled secondary antibody, or by a one-step method comprising contacting the sample <and the secondary antibody simultaneously with the primary antibody. The one-step method is advantageous over the two-step method because it permits a simpler and more rapid determination of human protein S.

In the two-step method, the fixed primary antibody and the sample are contacted and reacted at a given temperature for a given period of time[During this time, the fixed primary antibody combines with the human protein S in the sample. After washing with a suitable washing liquor, the reaction product is contacted and reacted with a solution (e.g., an aqueous solution) of the labelled secondary antibody at a given temperature for a given period of time. The reaction product is washed with a suitable washing liquor, and the amount of the labelling substance present on the insoluble solid carrier is measured. The amount of the human protein S in the sample can be determined by comparing the amount of the labelling substance with a calibration curve drawn by using an assay sample containing human protein S in a known concentration.

In the one-step method, the fixed primary antibody is contacted and reacted with the assay sample and the labelled secondary antibody simultaneously, preferably with a mixture of the sample and the labelled secondary antibody, at a given temperature for a given period of time. The product is then washed with a suitable washing liquor, and the amount of the labelling substance present on the insoluble solid carrier is measured as described above. As a result, the amount of human protein S in the sample can be determined.

According to the methods described above, the amount of human protein S in the assay sample can be measured easily with good reproducibility and a high accuracy. Human plasma, human serum and a supernatant from a cell culture are examples of the sample which can be assayed by the above methods.

For the practice of the above method, the present invention provides a reagent system comprising the primary antibody fixed to the insoluble solid carrier and the labelled secondary antibody. A kit may be formed from this reagent system and various auxiliary agents in order to use the reagent system efficiently and easily. Examples of the auxiliary agents include dissolving agents for dissolving the solid secondary antibody, washing agents for washing the insoluble carrier, substrates for measuring the enzyme activity of enzymes which may be used as labelling substances for the secondary antibody, and reaction stoppers therefor, which are normally used in reagent kits for immunological assay.

(2) Determination of a human C4bp-protein S complex in an assay sample by using the monoclonal antibody B:

The method of immunologically determining human C4bp-protein S complex in an assay sample according to this invention and the reagent system used therefor may be the same as the method and reagent system described in (1) above except that in the former reagent system, the monoclonal antibody B is used instead of the monoclonal antibody A, and a monoclonal or polyclonal antibody capable of recognizing and binding to C4bp is used instead of the monoclonal or polyclonal antibody which recognizes and binds to an epitope of human protein S different from that recognized by the monoclonal antibody A. Repetition of the description of the method will therefore be omitted.

(3) Monoclonal antibodies A and B and preparation thereof

The monoclonal antibody A or B can be obtained by establishing a hybridoma cell line capable of producing such antibody, and then cultivating the hybridoma.

The hybridoma capable of producing the monoclonal antibody A or B can be produced by a technique known as the Köhler and Milstein method [Köhler and Milstein, Nature, 256, 495–497 (1975)]. Specifically, a mammal such as a mouse is immunized with free human protein S, and antibody-producing cells, for example, spleen cells, of this animal are fused with meloma cells. The fused cells are screened by cloning for fused cells capable of producing the monoclonal antibody of this invention. For example, the fused cells produced are systematically screened for an antibody which reacts with free human protein S or human C4bp-protein S complex fixed to microtiter plates. A hybridoma in accordance with the present invention is on deposit with Fermention Research Institute in Japan under accession number FERM BP-2624.

The monoclonal antibody A or B can be obtained from the product yielded by this hybridoma. The resulting monoclonal antibody acts monospecifically on the epitope of free human protein S or C4bp-protein S complex.

The monoclonal antibody A or B and a process for producing it will now be described in more detail.

(A) Isolation and purification of an antigen

Free human protein S used as an antigen is isolated in pure form from a human plasma sample by the method of BaJaj et al. BaJaj S. P, Rapaport S. I., Maki S. L., Brown S. F.: Prep. Biochem., 13. 191, (1983)).

(B) Immunization of mammals with free human protein S

There is no particular restriction on the animals to be immmunized, and various mammals such as mice, rats, guinea pigs, rabbits, sheep, goats, dogs and cats may be used. For ease of handling, male Balb/c mice are generally used. Mice of other strains may also be used. The immunization should be planned, and the concentration of free human protein S to be used in immunization should be selected, so that sufficient amounts of antigenically stimulated lymphocyte can be formed. For example, a mouse is intraperitoneally immunized several times with a small amount of free human protein S at certain intervals, and the antigen is further administered intravenously several times to increase the titer of the antibody. Several days after the final immunization, antibody-producing cells, for example, lymphocytes, preferably spleen cells, are taken out from the immunized animals. The following description is given with regard to the use of spleen cells as the antibody-producing cells, but it should be understood that other antibodyproducing cells isolated from immunized animals can equally be used for cell fusion.

(C) Cell fusion

The spleen is aseptically taken out from the immunized animal, and a spleen cell suspension is prepared from it. The spleen cells are then fused with myeloma cells taken from a suitable cell line n a fusion medium in the presence of a suitable fusion promoter. The myeloma cells used for fusion may be obtained from any mammals, but generally, those originated from the same kind of animal as the immunized animal are preferred. The preferred mixing ratio of the spleen cells to the myeloma cells is generally in the range of from about 20:1 to about 2:1, preferably from 10:1 to 2:1 Usually, the use of 0.5 to 1.5 ml of the fusion medium per about $10^8$ spleen cells is suitable. Suitable fusion media are, for example, physiological saline, buffered saline, and a serum-free medium each of which contains the fusion promoter in a concentration of 30 to 70%.

Many myeloma cells suitable for cell fusion are known. In Examples to be given hereinafter, P3-X63-Ag8-Ul cells (to be abbreviated as P3-Ul) se D. E. Yelton et al.: Current Topics in Microbiology and Immunology, 81, 1 (1978)] are used. They are an 8-azaguanine resistant cell line. They lack hypoxanthine-guanine phosphoibosyl transferase, and therefore do not survive in HAT medium (containing hypoxanthine, aminopterin and thymidine). Furthermore, since this cell line is of a non-secreting type which does not secrete an antibody itself, it is suitable for the production of the hybridoma contemplated by the present invention. Other myeloma cells may also be used. Examples include P3-NSl-1-Ag4-1, NSl-A4/1, P3-X63-Ag8, (MPCH-45, 6. TGl.7), SP2/0-Agl4, OF, X-63-Ag8-6.5.3, 210.RCY3.Agl.2.3, S194/5XXO.BU.1, SKO-007, and GM15006TG-A12.

Polyethylene glycol having a average molecular weight of 1,000 to 4,000, for example, may be advantageously used as the fusion promoter. There can also be used other fusion promoters known in the art, such as Sendai virus. In the following Examples, polyethylene glycol having an average molecular weight of 540 was used.

(D) Detection of the fused cells

A mixture of the fused cells non-fused spleen cells and non-fused myeloma cells is diluted in a separate receptacle (such as a microtiter plate) with a selective medium in which the non-fused myeloma cells cannot survive, and cultivated for a sufficient period of time to allow the non-fused cells to die (about 1 week). The culture medium may be one which is resistant to a drug such as 8-azaguanine and in which the "on-fused myeloma cells cannot survive, for example the aforesaid HAT medium. In the selective medium, the "on-fused myeloma cells die away. Since the non-fused spleen cells are non-tumoral, they die after a certain period of time (about 1 week). On the other hand, the fused cells can survive in the selective medium because they have both the tumor-bearing nature of the parent myeloma cells and the nature of the parent spleen cells.

(E) Determination of an antibody to free human protein S in each receptacle:

After the hybridoma cells are detected as stated above, the supernatant of the culture fluid is collected, and screened for an antibody to free human protein S or C4bp-protein S complex by enzyme linked immunosorbent assay (see, for example, A. H. W. M. Shuurs and B. K. van Weemen: Clin. Chim. Acta, 81, 1–40 (19/7)].

(F) Cloning of the hybridoma capable of producing the antibody A or B

The hybridoma capable of producing the desired antibody can be cloned by a suitable method such as a limiting dilution method in two different ways. In one way, the hybridoma is cultivated in a suitable medium for a given period of time, and the monoclonal antibody produced by the hybridoma can be obtained from the supernatant of the culture fluid. In the other, the hybridoma can be intraperitoneally injected into a syngenic mouse. After a certain period of time, the monoclonal antibody A or B produced by the hybridoma can be obtained from the blood and ascites of the host animal.

(G) Properties of the monoclonal antibodies A and B

The monoclonal antibody A produced as above has an isoelectric point in the range between a pH of 6.2 and 6.8 and binds selectively only to free human protein S. The class of its H-chains is $\gamma_1$, and the class of its L-chains is $\kappa$. Its dissociation constant (KD), measured by the method of Frankel and Gerhard [Frankel, M. E., Gerhard, W.: Mol. Immunol. 16, 107 (1979)], is $0.5-1.5 \times 10^{-9}$ M with respect to free protein S, but cannot be measured with respect to C4bp-protein complex because it does not substantially bind to the complex.

The monoclonal antibody B has an isoelectric point in the range between a pH of 5.6 and 6.2, and binds selectively only to C4bp-protein S complex (namely does not substantially bind to free protein S nor to C4bp). The class of its H-chains is $\gamma_{2b}$, and the class of its L-chains is $\kappa$. The dissociation constant (KD) of the monoclonal antibody B, measured by the method of Frankel and Gerhard, is $4.0-6.0 \times 10^{-8}$ M with respect to free protein S, and $1.0-2.0 \times 10^{-9}$ M with respect to C4bp-protein S complex. Its dissociation constant with respect to C4bp cannot be measured because it does not substantially bind to C4bp (the dissociation constant with respect to free protein S cannot be measured by the EIA method because it is outside the detection limit).

Litwiller et al. [1] and Malm et al. [2] separately reported monoclonal antibodies to human protein S specific for a $Ca^{2+}$-stabilized epitope R. D. Litwiller, R. J. Henny, J. A. Katzmann. R. S. Miller, and K. G. Mann: Blood, vol. 67, No. 6, pp. 1583–1590 (1986); [2] J. Malm, U. Persson and B. Dahlback. European Journal of Biochemistry, vol. 165, pp. 39–45 (987)]. The epitopes for these monoclonal antibodies are located in the Gla region of protein S or in a closely positioned thrombin-sensitive region. These monoclonal antibodies recognize both free protein S and the C4bp-protein S complex. The present invention provides the monoclonal antibodies A and B. The monoclonal antibody A recognizes only free protein S, and does not bind to the C4bp-protein S complex, whereas the monoclonal antibody B recognizes the C4bp-protein S complex specifically. This fact demonstrates that the monoclonal antibodies A and B are different and distinguished from the monoclonal antibodies of Litwiller et al. and Malm et al.

The monoclonal antibody A in accordance with this invention can also be applied to the separation or recovery of free human protein S from liquid containing the free human protein S because it has the function of specifically binding to the epitope of the free human protein S.

Thus, according to still another aspect of this invention, there are provided a selective adsorbent for free human protein S comprising an insoluble solid carrier and the monoclonal antibody A fixed thereto, and a method for separating or recovering free human protein S from a liquid containing free human protein which comprises bringing the liquid containing free human protein S into contact with the selective adsorbent to cause free human protein S to be adsorbed on the adsorbent, and separating the adsorbent from the liquid, and as required, desorbing free human protein S from the adsorbent and recovering it.

Generally, chromatography based on the utilization of the biological affinity of an adsorbent to the separation and purification of a biological substance is called affinity chromatography [Ichiro Chihata, Tetsuya Tosa and Yushi Matsuo, "Experimental and Applied Affinity Chromatography" (Japanese-language publication), Kodansha Co., Ltd.].

The terms "affinity", "ligand", "insoluble solid carrier", and "adsorbent", as used herein, should be understood to have the following meanings.

Affinity: specific affinity between two substances.

Ligand: a substance having affinity for a substance to be adsorbed or purified.

Insoluble solid carrier: a solid support insoluble in water (excluding the ligand).

Adsorbent: the insoluble solid carrier to which the ligand is fixed.

Now, the selective adsorbent for human protein S and the method for separating or recovering human protein S from a liquid containing the human protein S, which are provided by this invention, will be described in detail.

The monoclonal antibody A to human protein S or its Fab region-containing fragment in accordance with this invention is chemically bonded as to a suitable insoluble carrier (e.g., Sepharose), and the carrier is then packed into a column. The column is equilibrated with a suitable buffer (for example, 50mM Tris buffer, pH 7.4, 0.15 M NaCl). A liquid containing human protein S to be treated (such as a human plasma or serum sample) is added to the resulting adsorbent to adsorb human protein S on the adsorbent. Impurities are then removed from the adsorbent by a suitable washing solution (for example, 50mM Tris buffer, pH 7.4, 0.15 M NaCl) Then, the amount of human protein S in a fraction which has passed through the column ("pass-through fraction") and a fraction which has been washed out from the column ("washed fraction") is measured. From the measured values, the degree of separation of human protein S from the sample liquid can be calculated.

Various substances can be used as the insoluble solid carrier used in the selective adsorbent of this invention. Preferably, it is made of, for example, agarose, polyacrylamide, cellulose, dextran, maleic acid polymer, or a mixture thereof. The insoluble solid carrier may be in various forms, for example, in the form of a powder, granule, pellets, beads, film or fiber.

Fixation of the monoclonal antibody or its fragment to the insoluble solid carrier is generally carried out by chemically bonding it to the carrier. For example, it may be effected by activating Sepharose by the action of CNBr and fixing the antibody to it R. Axan et al.: Nature, 214, 1302–1304 (1967)].

When the adsorbent having human protein S adsorbed thereon by contact with the liquid containing human protein S is separated from the liquid, the human protein S present in the liquid can be removed If human plasma or serum is used as the liquid, human plasma or serum substantially free from human protein S can be obtained. Such human protein S-free human plasma or serum can be advantageously used, for example, in plasma or serum exchange therapy.

The adsorbent having human protein S adsorbed thereon and separated from the assay liquid may be subjected to a desorption treatment to elite human protein S from the adsorbent and recover it. The recovered human protein S can be used, for example, as a supplement in congenital protein S deficiency disease and liver diseases, or as a hemostat. The desorption treatment may be carried out by treating the adsorbent having human protein S adsorbed thereon with an eluent. An aqueous solution of sodium thiocyanate having a pH of 2.5 to 12.5, preferably 4.0 to 9.0, can be advantageously used as the eluent. Other examples of the eluent that can be used in the invention include an aqueous solution of glycerol, an aqueous solution of glycine, an aqueous solution of propionic acid, an aqueous solution of ethylene glycol, and an aqueous solution of guanidine.

The concentration of sodium rhiocyanate in the aqueous sodium thiocyanate solution is advantageously 0.5 M to 6 M, preferably 2 M to 4 M. For pH adjustment, the aqueous solution may include suitable pH-adjusting agents, for example hydroxides such as sodium hydroxide or potassium hydroxide, salts such as Tris sales, phosphate salts or Veronal salt, acids such as hydrochioric acid, nitric acid, acetic acid, citric acid and oxalic acid, amines such as ethanolamine, ammonia, or urea The desorption treatment is carried out at a temperature above the freezing point but not exceeding 37° C., preferably at 2° to 10° C. The desorption treatment is performed by a column method, a batch method, etc. The time required for elution is desirably short, but may be up to about 2 days.

From the eluate containing the eluted human protein S, the human protein S can be separated and purified by methods known per se, for example by dialysis, concentration, or liquid chromatography.

As stated hereinabove, the monoclonal antibody A or its Fab region-containing fragment has the function of specifically blocking the C4bp binding site of human protein S, i.e. that site of human protein S which binds C4b-binding protein (C4bp). Human protein S exists in plasma in two forms. One is the free protein S, and the other is the C4bp-protein S complex. Only the free protein S serves as a cofactor in the inactivation of coagulation factors Va and VIIIa by activated protein C, which is a vitamin K-dependent serine protease. The function of these cofactors are lost when protein S binds to C4b-binding protein. When the monoclonal antibody A in accordance with this invention binds to protein S, the C4b-binding protein (C4bp) cannot bind to the protein S-monoclonal antibody-immunocomplex, but the immunocomplex serves as a cofactor of activated protein C.

The monoclonal antibody A or its Fab regioncontaining fragment in accordance with in this invention can therefore be used for the treatment of human thrombotic diseases including myocardial infarction, cerebral infarction, vein obstructive diseases and artery obstructive diseases.

The monoclonal antibody A or its fragment used in the invention may be administered parenterally, preferably intravenously. The dose varies depending upon the sex, age, condition, body weight, etc. of a patient to be treated. Generally, the dose may be about 0.01 to about 10 mg/kg of body weight daily as an amount effective for dissolving thrombus either once or several times a day. By the judgement of a physician, it may, of course, be administered in higher doses.

The monoclonal antibody A or its fragment may be formulated into a form suitable for administration, for example an injectable solution, a drip, a lyophilized powder, together with a pharmaceutically acceptable carrier or diluent. Examples of the pharmaceutically acceptable carrier or diluent are water, buffers, blood isotonizing agents, stabilizers (e.g., human plasma albumin, mannitol), and human antibodies or their fragments. An injectable solution or a drip may be prepared by dissolving the monoclonal antibody A or its fragment of this invention in physiological saline in a concentration of 0.001 microgram/ml to 100 ng/ml, and as required, further adding 0.01 M sodium phosphate as a buffer, and 1% of mannitol and 0.1% of human serum albumin as stabilizers. The concentrations of the additional agents may be varied properly. As required, a human antibody or its fragment may be added. The injectable solution or drip may be prepared in the form of a solution or in a lyophilized form. The lyophilized product may be dissolved in such a medium as deionized water before use. The injectable solution, the drip, a lyophilized product thereof, and a solution of the lyophilized product should be prepared and stored aseptically.

BRIEF DESCRIPTION OF THE ACCOMPANYING DRAWINGS

Figure 1:
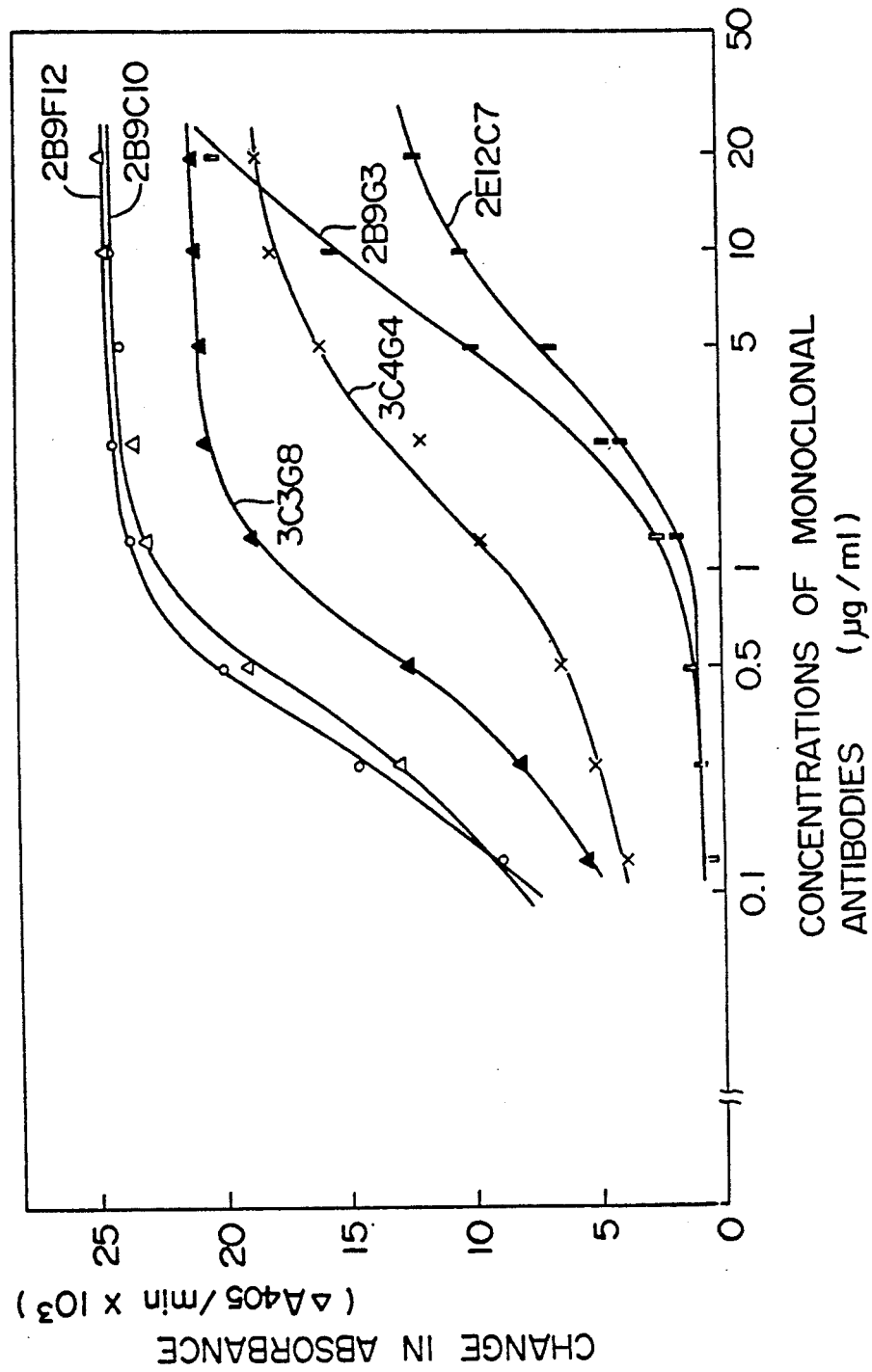
FIG. 1 shows the strengths of binding of the monoclonal antibodies of this invention to human protein S.

The following Examples illustrate the present invention in greater detail. In these Examples, protein S is sometimes abbreviated as "PS".

EXAMPLE 1

Two female Balb/C mice (four weeks old) were immunized four times with purified human PS at 14-day intervals. In the first immunization, 50 micrograms of human PS dissolved in PBS was mixed with an equal quantity of complete Freund's adjuvant, and the resulting emulsion was intraperitoneally administered (0.5 mg/head). In the second and third immunizations, 50 micrograms of human PS was mixed similarly with Freund's incomplete adjuvant, and intraperitoneally administered. In the final immunization, 30 micrograms of human PS in PBS was directly administered through the tail vein. Three days after the final immunization, the spleen cells of the immunized mice were used in cell fusion.

The spleen cells of the immunized mice and myeloma cells (P3U1) of mice of the same strain were mixed at a ratio of from about 5:1 to about 7:1 and fused in accordance with the method of Kohler and Milstein in the presence of 50% ethylene glycol 1540 (a product of Wako Pure Chemicals Co., Ltd.). The fused cells were suspended in 10% FCS-RPM1-1640 medium so that the cell concentration was $1 \times 10^6$ cells/ml The suspension was poured onto a 95-well microplate (made by Coster Company) at a rate of 100 microliters per well.

The fused cells were cultivated in a CO$_2$ incubator (5% CO$_2$, 37° C). The medium was replaced by a medium containing hypoxanthine, aminopterin and thymidine (HAT medium), and the cells were grown in the HAT medium. Hybridomas composed of the spleen cells and the myeloma cells were screened.

The antibodies in the supernatant of the culture fluid of the hybridoma were detected by the ELISA method using microtiter plates coated with antigen human PS. Alkaline phosphatase-conjugated rabbit anti-mouse IgG antibody was used as a second antibody, and the bindability of the antibodies to the antigen PS was examined. Among 494 wells in total in which the fused cells had been seeded, formation of colonies was observed in 487 wells. Of these, 94 wells were positive in antibody production showing the ability to bind to the antigen PS.

On four wells out of the positive wells, cloning was carried out twice by the limiting dilution method, and six clones were obtained. The clones obtained were suspended in 90% FCS-10% DMSO and stored in liquid nitrogen.

Monoclonal antibodies produced by these clones were grown in the abdominal cavities of Balb/C mice, and purified from the ascites of the mice using a protein A-Sepharose 4B column.

TABLE 1

| | (cell fusion) | | |
|---|---|---|---|
| | Cell fusion 1 | Cell fusion 2 | Total |
| Spleen cells (per ml) | $1.15 \times 10^7$ | $6.70 \times 10^6$ | |
| Myeloma cells (per ml) | $1.72 \times 10^6$ | $1.33 \times 10^6$ | |
| Ratio of spleen cells/myeloma cells | 6.0 | 5.0 | |
| Number of cells per well | $0.57 \times 10^5$ | $0.67 \times 10^5$ | |
| Number of wells | 302 | 192 | 494 |
| Wells positive in colony formation | 298 (98.6%) | 189 (98.4%) | 487 (98.6%) |
| Wells positive in antibody production | 66 (21.8%) | 28 (14.8%) | 94 (19.0%) |

EXAMPLE 2

Properties of the purified monoclonal antibodies

The clones purified from the mouse ascites were examined for IgG classes and bindability to human protein S (PS).

The particular classes of the mouse monoclonal antibodies were determined by the Ouchterlony method using anti-mouse anti-sera specific for the individual classes.

The results are shown in Table 2.

The bindability of the antibodies to human protein S was evaluated by reacting human protein S fixed to microtiter plates with the monoclonal antibodies diluted to suitable concentrations and detecting the reaction products by using alkaline phosphatase-conjugated goat anti-mouse IgG.

The strengths of binding of the six monoclonal antibodies to human protein S are: 2B9F12≈B2B9C10>3C3G8>3C4G4>2B9G2>>2-E12C7.

The results are shown in FIG. 1.

TABLE 2

| Monoclonal antibody | Class |
|---|---|
| 2B9F12 | IgG$_1$ |
| 2B9C10 | IgG$_1$ |
| 3C3G8 | IgG$_3$ |
| 3C4G4 | IgG$_1$ |
| 2B9G3 | IgG$_1$ |
| 2E12C7 | IgG$_{2b}$ |

EXAMPLE 3

Reactivity with human C4b-binding protein and protein S complex (C4bp-PS complex)

Three purified monoclonal antibodies (2B9F12, 2B9C10, 2E12C7) and goat anti-PS antibody were coated on microtiter plates in a concentration of 10 micrograms/ml, and blocked with 1% BSA. Then, the C4bp-protein S complex diluted to a suitable concentration was added and reacted with the monoclonal antibodies. Then, alkaline phosphatase-conjugated anti-C4bp antibody was added and the bindabilities of the three monoclonal antibodies to the C4bp-protein S complex were detected.

Monoclonal antibody 2E12C7 had very weak bindability to free protein S, but showed a high degree of specific bindability to the C4bp-protein S complex. On the other hand, 2B9F12 did not show bindability to the C4bp-protein S comlex.

Figure 2:
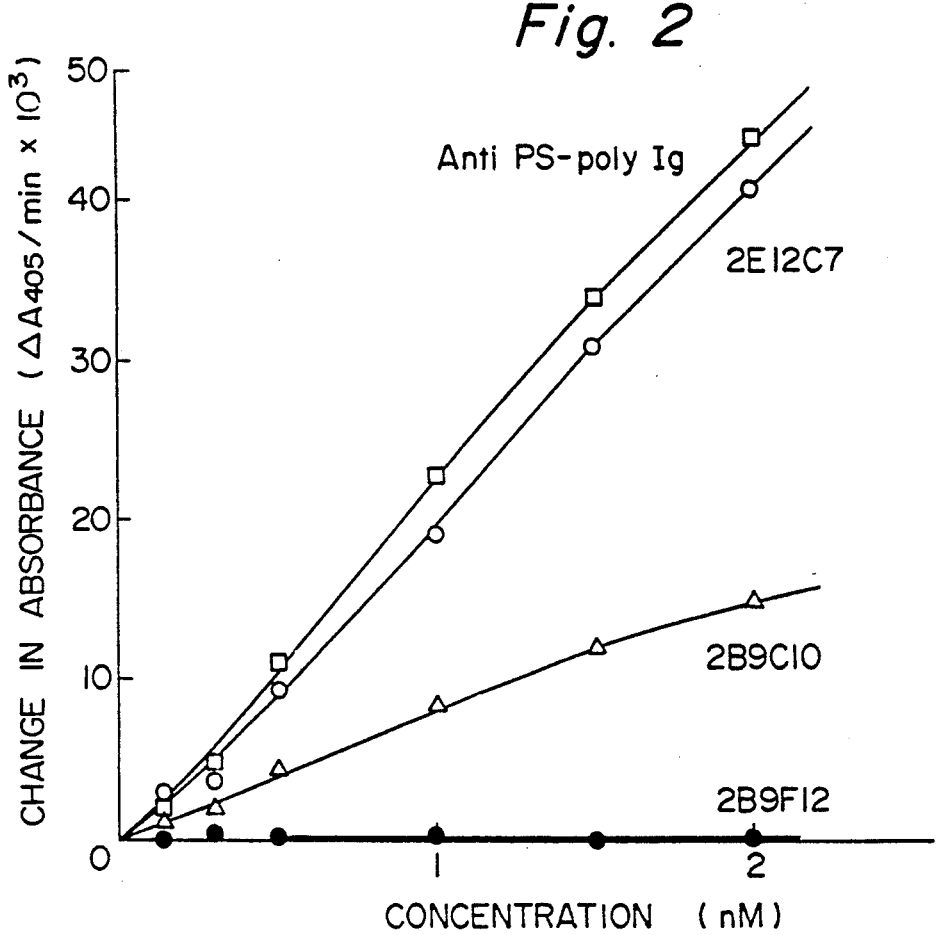
FIG. 2 shows the strengths of binding of the monoclonal antibodies of this invention to the C4bp-protein S complex.

The results are shown in FIG. 2

In this way, by using various antibodies in immunological assaying means (EIA, RIA), free human protein S and C4bp-protein S complex in solution (for example, human plasma) can be assayed.

EXAMPLE 4

Measurement of dissociation constants (KD):

A purified monoclonal antibody was labelled with $^{125}I$ (iodine-125) by using Immunobeads (a product of Bio-Rad Co.).

Purified protein S and C4bp-protein S complex in a concentration of 1 microgram/ml were added to a 96-well microtiter plate (Titertek made by Flow Lab. Co.) at a rate of 50 microliters/well, and adsorbed at 4° C. overnight. 10 mM phosphate buffer (pH 7.2) containing 1% and 0.125 M NaCl was added at a rate of 100 microliters/well. The plates were then left to stand at room temperature for 2 hours, and then washed twice (100 microliters/well) with 10 mM phosphate buffer (pH 7.2) containing 0.05% Tween 20 (washing solution). The $^{125}I$-labelled monoclonal antibody diluted to various concentrations (0.01 to 5 micrograms/ml) was added to the wells of the plate and incubated at 37° C. for 2 hours. The plate was then washed three times with the above washing solution (100 microliters/well). The wells were cut out from the plate and put in plastic test tubes. The $^{125}I$-radioactivity was measured by a gamma counter (radioactivity bound to the solidified antigen: B in cpm). At the same time, the radioactivity of the diluted solution of $^{125}I$-labelled monoclonal antibody solution added to the wells was measured (the total added radioactivity: T in cpm). The concentration of the added monoclonal antibody was taken on the axis of abscissa, and the ratio between T-B (the radioactivity not bound to the solidified antigen: F in cpm) and B, on the axis of ordinates. From the Scatchard plot, the dissociation constant (KD) was calculated. The results are summarized in Table 3.

TABLE 3

| Antibody | PS KD (mole/liter) | PS-C4bp (KD (moles/liter) |
|---|---|---|
| 2B9F12 | $1.03 \times 10^{-9}$ | Not detected |
| 2B9C10 | $4.89 \times 10^{-9}$ | $7.29 \times 10^{-8}$ |
| 2E12C7 | $5.71 \times 10^{-8}$ | $1.84 \times 10^{-9}$ |

EXAMPLE 5

Figure 3:
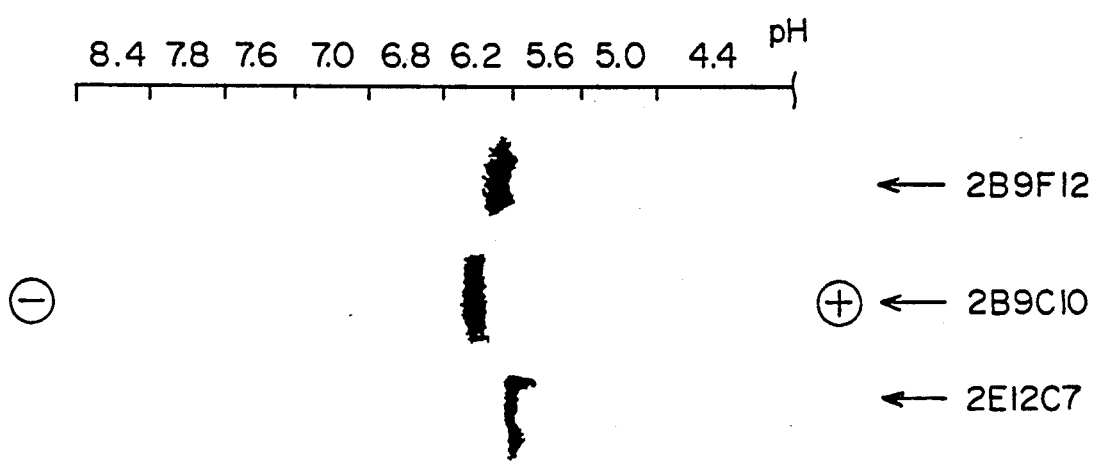
FIG. 3 shows the isoelectric points of the monoclonal antibodies of the invention.

Measurement of the isoelectric points of purified monoclonal antibodies:

Each of purified monoclonal antibodies (2B9F12, 2B9C10 and 2E12C7) in an amount of 20 micrograms was subjected to agarose isoelectric focusing at 4° C. under a pH gradient of 3.5 to 9.0. After isoelectric focusing for 2 hours, the antibody protein in the agarose gel was immobilized and stained with CBB. The photograph of this electrophoresis was taken and shown in FIG. 3. From the positions of the electrophoretic bands of the monoclonal antibodies, the isoelectric points of the antibodies were measured using a standard isoelectric point marker electrophoresed simultaneously. They were a pH of 6.2 to 6.8 for 2B9F12, a pH of 6.2 to 6.8 for 2B9C10, and a pH of 5.6 to 6.2 for 2E12C7.

EXAMPLE 6

(1) Fixing of an antibody to an insoluble carrier

A dry gel (0.5 g) of cyanogen bromide-activated Sepharose 4B (made by Pharmacia Fine Chemicals, Inc.) was swollen and washed with 100 ml of 1 mM HCl and then further washed with a coupling buffer (0.1 M NaHCO$_3$ containing 0.5 M NaCl, pH 8.3) on a G3 glass filter. The coupling buffer was removed by suction, and immediately then, the gel was suspended in 2 ml of a coupling buffer solution (3 mg/ml) for a monoclonal antibody (2B9F12). The suspension was gently shaken overnight at 4° C. The gel was then transferred to 1 M ethanolamine-HCl (pH 8.0, 2 ml) and shaken at room temperature for 2 hours to block the remaining active groups. After the blocking, the antibody-bound Sepharose gel was washed on a glass filter with 0.1 M acetate buffer (pH 4.0) containing 0.5 M NaCl and 0.1 M borate buffer (pH 8.0) containing 0.5 M NaCl alternately. When the absorbance of the filtrate at 280 nm decreased below 0.01, it was equilibrated with 0.05 M Tris/HCl (pH 7.4) containing 1 mM benzamidine, and filled in a column. Affinity chromatography was performed on the prepared anti-human PS monoclonal antibody (2B9F12)-bound Sepharose 4B column.

(2) Adsorption of protein S on antibody-bound Sepharose 4B and elution thereof

To 100 ml of plasma was added to 8 ml of 1M BaCl$_2$ solution, and the mixture was stirred at 4° C. for 1 hour. The precipitate was collected by centrifugal separation, and washed with 0.1 M NaCl containing 5 mM BaCl$_2$ and 5 mM benzamidine. The precipitate was dissolved in 15 ml of 0.2 M EDTA (pH 7.4) containing 5 mM benzamidine to obtain a barium adsorbed fraction. The barium-adsorbed fraction was dialyzed against 0.05 M Tris/HCl (pH 7.4) containing 1 mM benzamidine and applied to the antibody 2B9F12-bound column equilibrated with 0.05M Tris/HCl (pH 7.4) containing 1 mM benzamidine. The column was washed with 0.05 M Tris/HCl (pH 7.4) containing 1 mM benzamidine and 1 M NaCl and eluted with 3 M NaSCN (pH 7.0) solution. A single peak containing PS was obtained. The recovery ratio was about 75.4%.

EXAMPLE 7

Figure 4:
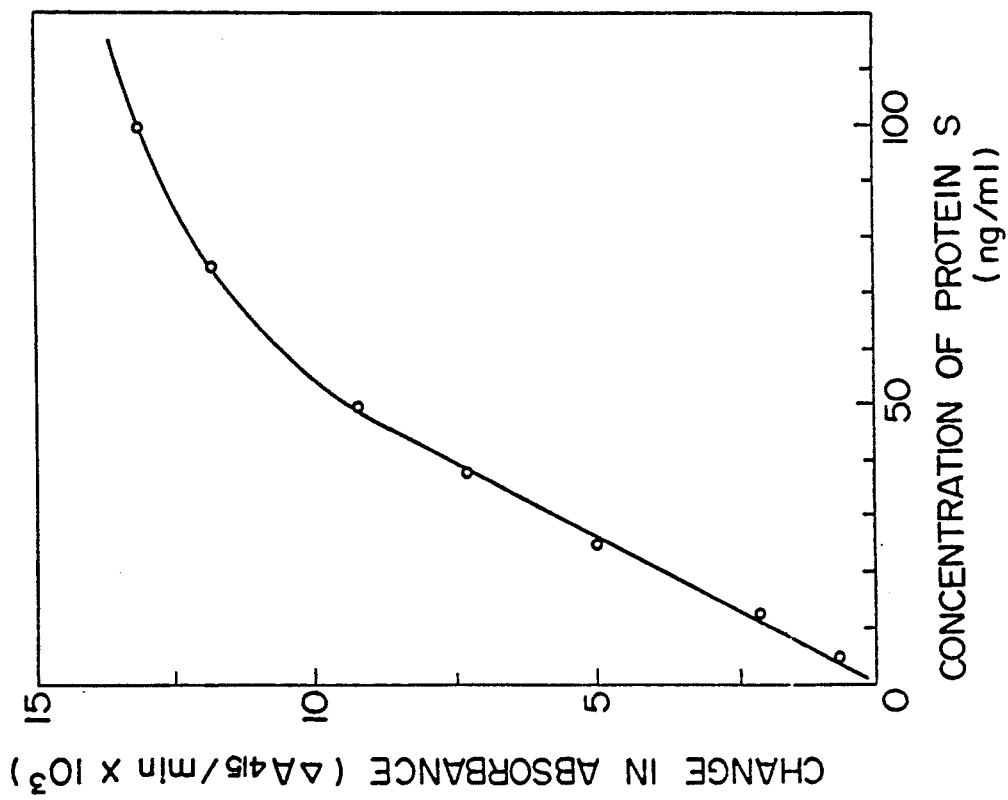
FIG. 4 is a calibration curve showing the relation between the concentration of human protein S and changes in absorbance.

Measurement of human protein S:

The monoclonal antibody obtained in Example 1 (2B9F12) to human protein S was coated on a microtiter plate in a concentration of 15 micrograms/ml. The plate was blocked with phosphate buffer (PBS) containing 1% bovine serum albumin (BSA), and then washed three times with a washing solution (0.5% BSA-PBS containing 0.05% of Tween). Then, purified protein S and a plasma sample taken from a human patient were diluted to suitable concentrations with PBS and reacted at 37° C. for 2 hours with the monoclonal antibody adsorbed on the solid phase of the plate. The plate was washed three times with the washing solution, and then a solution of a peroxidase-labelled monoclonal antibody (2B9C10) to human protein S was added. The plate was incubated at 37° C. for 2 hours, and washed with the washing solution three times. Then, a substrate (ABTS) solution was added, and changes in absorbance per minute ΔA415 nm/min.) was measured by an ELISA ANALYZER (ETY-96 made by Toyo Sokki Co., Ltd.). The concentrations of purified protein S and the changes in absorbance were plotted to draw a calibration curve. The calibration curve is shown in FIG. 4. The concentration of protein S and the absorbance was in a straight-line relationship up to about 50 ng/ml. If this calibration curve is used, the amount of human protein S can be accurately calculated with high sensitivity.

Figure 6:
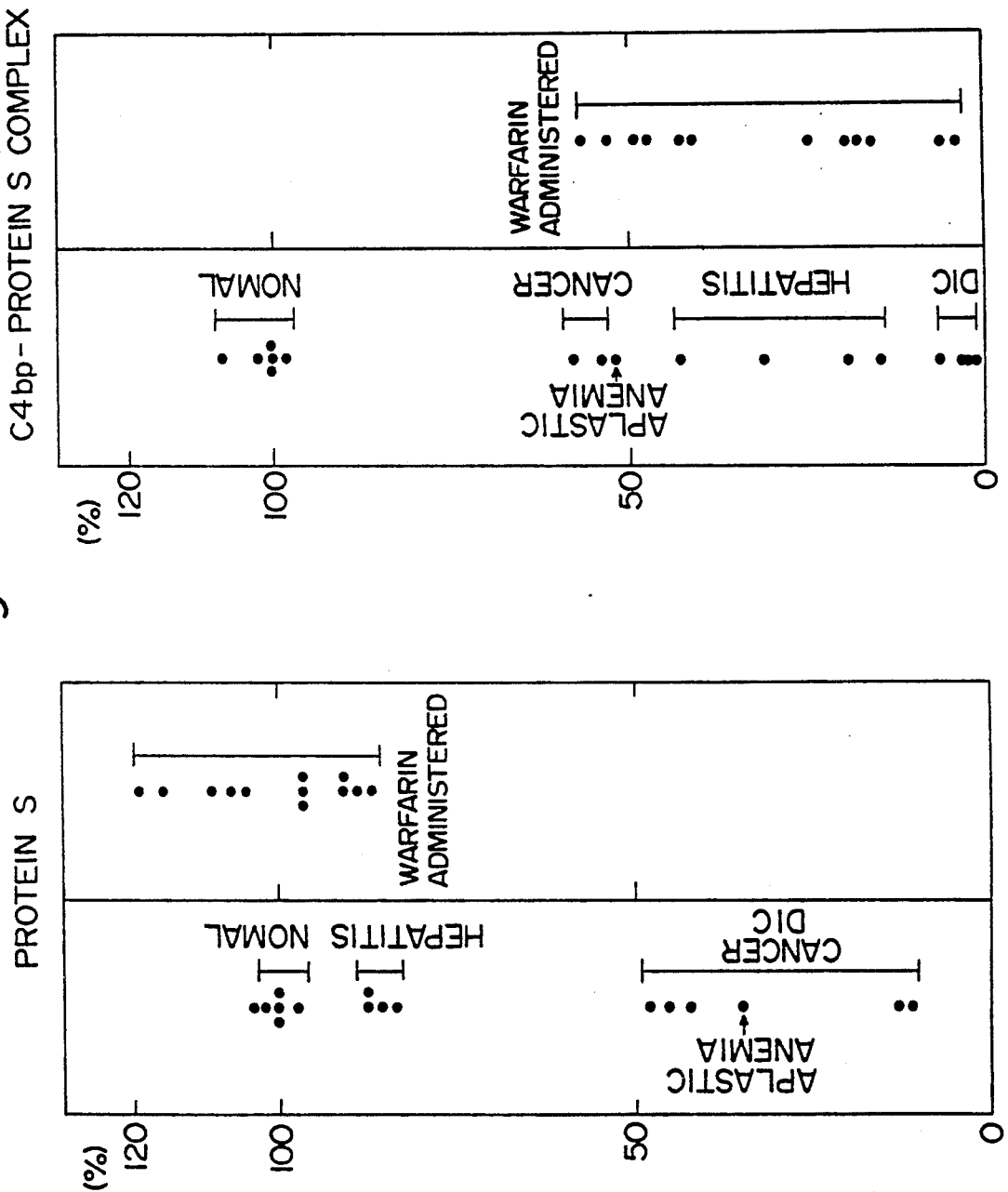
FIG. 6 shows the actual measured amounts of human protein S and human C4bp-protein S complex in plasma samples taken from human patients.

The amount of protein S in plasma samples of human patients was calculated by using this calibration curve, and the results are shown in FIG. 6. In FIG. 6, the amount of protein S in a plasma sample taken from a normal healthy subject is indicated as 100%.

EXAMPLE 8

Measurement of the human C4bp-protein S complex

The monoclonal antibody (2E12C7) to human protein S which bound specifically to the human C4bp-protein S complex was coated in a concentration of 20 micrograms/ml on a microtiter plate. The plate was blocked with phosphate buffer (PBS) containing 1% bovine serum albumin (BSA) and then washed three times with a washing solution (0.5% BSA-PBS containing 0.05% of Tween 20).

Figure 5:
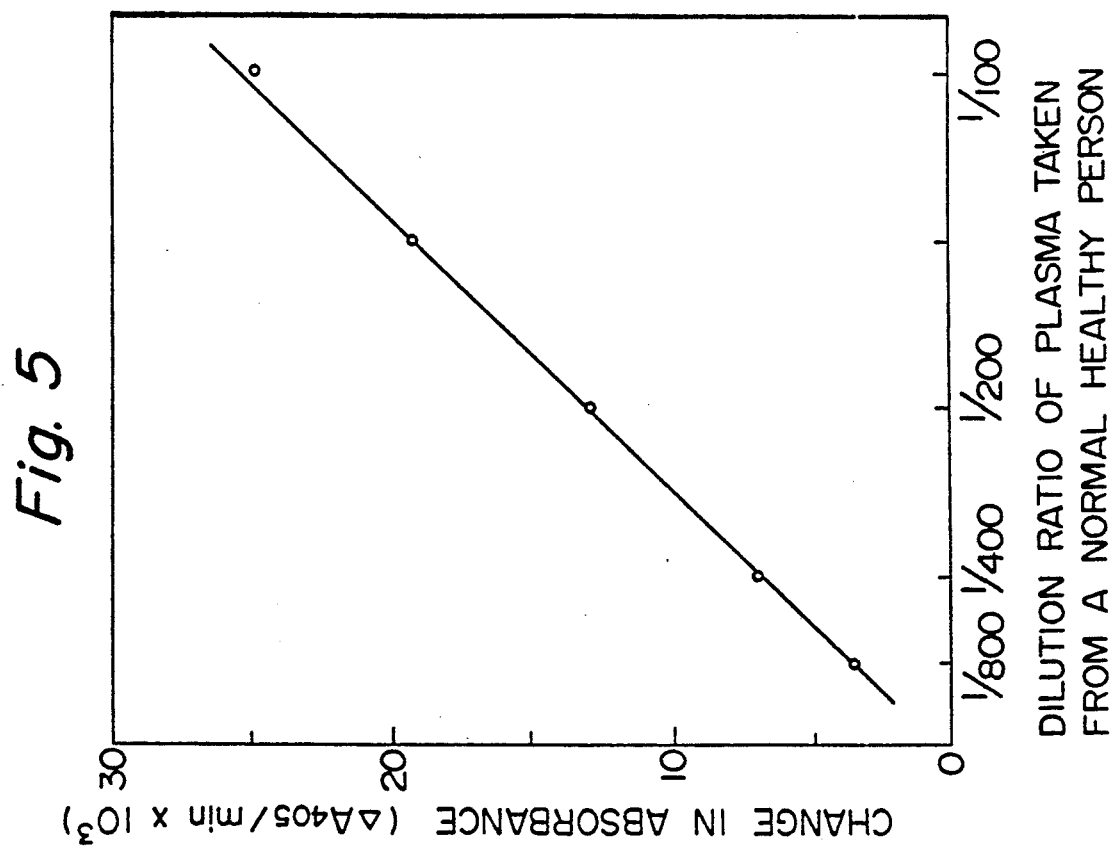
FIG. 5 is a calibration curve showing the relation between the amount of the human C4bp-protein S complex and changes in absorbance.

A plasma sample taken from a normal healthy person and plasma samples taken from patients were diluted to suitable concentrations with PBS, and each reacted at 37° C. for 2 hours with the monoclonal antibody adsorbed on the solid phase of the plate. The plate was washed three times with the washing solution, and reacted with a solution of an alkaline phosphatase-labelled polyclonal antibody to human C4b-binding protein (C4bp) at 37° C. for 2 hours. The plate was then washed three times with the washing solution, and a substrate solution (1 mg/ml) was added. Changes in absorbance per minute (ΔA405 nm/min.) were measured by an ELISA ANALYZER (ETY-96, made by Toyo Sokki Co., Ltd.). The plasma of a healthy person was diluted, and the amount of the human C4bp-protein S complex on the plasma and the changes in absorbance were plotted to draw a calibration curve. The calibration curve is shown in FIG. 5. The concentration of the human C4bp-protein S complex in the plasma of the healthy person and the changes in absorbance were in a straight-line relationship. The use of this calibration curve permitted accurate calculation of the amount of the human C4bp-protein S with high sensitivity.

The amount of the human C4bp-protein S complex in the plasma samples of human patients was calculated by using this calibration curve, and the results are shown in FIG. 6. In FIG. 6, the amount of the human C4bp-protein S complex in the plasma of the healthy person was indicated as 100%.

It is seen that various diseases can be diagnosed by determining the amounts of free protein S and C4bp-protein S complex in human plasma using monoclonal antibodies to human protein S.

We claim:

1. A method of immunologically determining free human protein S in an assay sample, which comprises contacting a primary antibody fixed to an insoluble solid carrier and a labelled secondary antibody with the assay sample, wherein each antibody binds to a distinct epitope of free human protein S, and either the primary or the secondary antibody, but not both, is a monoclonal antibody having a property of binding to free human protein S, and not binding to a complex of the human protein S and human complement cofactor C4b-binding protein (C4bp), said monoclonal antibody being produced by hybridoma FERM BP-2629 deposited in Fermentation Research Institute, Agency of Industrial Science and Technology, Japan and determinating the presence of said antibody.

2. A monoclonal antibody produced by hybridoma FERM BP-2629 deposited in Fermentation Research Institute, Agency of Industrial Science and Technology, Japan.

3. A hybridoma FERM BP-2629 deposited in Fermentation Research Institute, Agency of Industrial Science and Technology, Japan.

4. A reagent system for immunological determination of free human protein S in an assay sample, comprising a primary antibody fixed to an insoluble solid carrier and a labelled secondary antibody, wherein each antibody binds to a distinct epitope of free human protein S, and either the primary or the secondary antibody, but not both, is a monoclonal antibody having a property of binding to free human protein S and not binding to a complex of the human protein S and human complement cofactor C4b-binding protein (C4bp), said monoclonal antibody being produced by hybridoma FERM BP-2629 deposited in Fermentation Research Institute, Agency of Industrial Science and Technology, Japan.

5. The method of claim 1, wherein the assay sample contains free human protein S, a complex of the human protein S and human complement cofactor C4b-binding protein, and a human complement cofactor C4b-binding protein.

6. The method of claim 1 wherein the labelled secondary antibody is labelled with a member selected from the group consisting of an enzyme, a luminescent substance and a radioisotope.

7. The method of claim 1 wherein the labelled secondary antibody and the assay sample are contacted simultaneously with the primary antibody fixed to an insoluble solid carrier.

8. The reagent system of claim 4 wherein the insoluble solid carrier is a member selected from the group consisting of a plastic receptacle, plastic beads, glass beads and metal particles.

9. The reagent system of claim 4 wherein the labelled secondary antibody is the monoclonal antibody labelled with a member selected from the group consisting of an enzyme, a luminescent substance and a radioisotope.

10. A selective adsorbent for free human protein S comprising an insoluble solid carrier and the monoclonal antibody as set forth in claim 2 fixed thereto.

11. The selective adsorbent of claim 10 wherein the insoluble carrier is selected from the group consisting of agarose, polyacrylamide, cellulose, dextran, maleic acid polymer and a mixture thereof.

12. A method of separating or recovering free human protein S from a liquid containing the free human protein S, which comprises bringing the liquid into contact with an insoluble solid carrier to which the monoclonal antibody set forth in claim 2 is fixed to cause the free human protein S to be adsorbed on the carrier, and separating the carrier from the liquid, and optionally, desorbing the free human protein S from the carrier and recovering it.

13. The method of claim 12 wherein the liquid containing the free human protein S is a member selected from the group consisting of human plasma and serum.

14. The method of claim 12 wherein the desorption is carried out by using an aqueous solution of sodium thiocyanate having a pH of 4.0 to 9.0.

* * * * *